United States Patent
Wilk

(10) Patent No.: US 7,381,856 B2
(45) Date of Patent: Jun. 3, 2008

(54) CARBON-CARBON CROSS COUPLING CATALYZED BY TRANSITION METALS ON SOLID SUPPORTS

(75) Inventor: Bogdan Kazimierz Wilk, New City, NY (US)

(73) Assignee: Wyeth, Madison, NJ (US)

( * ) Notice: Subject to any disclaimer, the term of this patent is extended or adjusted under 35 U.S.C. 154(b) by 662 days.

(21) Appl. No.: 10/994,598

(22) Filed: Nov. 22, 2004

(65) Prior Publication Data

US 2005/0137438 A1    Jun. 23, 2005

Related U.S. Application Data

(60) Provisional application No. 60/524,554, filed on Nov. 24, 2003.

(51) Int. Cl.
*C07C 1/26* (2006.01)
*C07C 1/30* (2006.01)

(52) U.S. Cl. ..................................... 585/469
(58) Field of Classification Search ................. 585/469
See application file for complete search history.

(56) References Cited

U.S. PATENT DOCUMENTS

2003/0181748 A1    9/2003   Krauter et al.

FOREIGN PATENT DOCUMENTS

| EP | 1186583 A1 | 3/2003 |
|---|---|---|
| WO | WO-99/12940 A | 3/1999 |
| WO | WO-00/66164 A | 11/2000 |

OTHER PUBLICATIONS

Zhang et al., "6-Aryl-1,4-dihydro-benzo[d][1,3]oxazin-2-ones: a novel class of potent, selective, and orally active nonsteroidal progesterone receptor antagonists", J. Med. Chem., 45(20):4379-4382 (Sep. 26, 2002).
Courtois et al., "Catalysis by nickel-2,2'-dipyridylamine complexes of the electroreductive coupling of aromatic halides in ethanol", Tet. Lett, 40(30):5993-5996 (Sep. 16, 1999).
Andersen et al., "A Modified in Situ Suzuki Cross-Coupling of Haloarenes for the Preparation of $C_2$-Symmetric Biaryls", J. Org. Chem., 61:9556-9559 (1996).
Barnard et al., in Catalysis of Organic Reactions (M. Ford, Ed.) Marcel Dekker, Inc.: New York, 2001, 563-571.
Chamoin et al., "The Suzuki-Miyaura cross coupling reactions on solid support. Link to solution phase directed ortho metalation. The Leznoff acetal linker approach to biaryl and heterobiaryl aldehydes", Tetrahedron Lett. Jun. 11, 1998 39(24):4179-4182.
Dyer et al., "Preparation of enantiopure 4-arylmandelic acids via a Pd/C catalysed Suzuki coupling of enantiopure 4-bromomandelic acid", Tetrahedron Lett. Feb. 26, 2001 42(9):1765-1767.
Ennis et al., "Multikilogram-Scale Synthesis of a Biphenyl Carboxylic Acid Derivative Using a Pd/C-Mediated Suzuki Coupling Approach", Org. Proc. Res. Dev. Jul. 1999 3(4):248-252.
Fenger et al., "Reusable polymer-supported palladium catalysts: An alternative to tetrakis(triphenylphosphine)palladium in the Suzuki cross-coupling reaction", Tetrahedron Lett. Jun. 11, 1998 39(24):4287-4290.
Gala et al., "One-Step Synthesis of Biphenylacetic Acids via Pd/C-Catalyzed Arylation", Org. Proc. Res. Dev. Mar. 1997 1(2):163-167.
Hassan et al., "Aryl-aryl bond formation one century after the discovery of the Ullmann reaction", Chem. Rev. May 2002 102(5):1359-1470.
Heidenreich et al., "Control of Pd leaching in Heck reactions of bromoarenes catalyzed by Pd supported on activated carbon", J. Mol. Cat. A: Chemical May 31, 2002 182-183:499-509.
Jang et al., "Polymer-bound palladium-catalyzed cross-coupling of organoboron compounds with organic halides and organic triflates", Tetrahedron Lett. Mar. 10, 1997 38(10):1793-1796.
Kabalka et al., "Solventless Suzuki Coupling Reactions on Palladium-Doped KF/Al2O3", Org. Lett. Nov. 4, 1999 1(9):1423-1425.
Kaneda, K., "Green carbon-carbon bond-forming reactions by heterogeneous metal catalysts" J. Synth. Organ. Chem. Japan May 2003 61(5):436-444 [Abstract].
Kogan et al., "Carbon-Carbon and Carbon-Nitrogen Coupling Reactions Catalyzed by Palladium Nanoparticles Derived from a Palladium Substituted Keggin-Type Polyoxometalate", Org. Lett. Oct. 3, 2002 4(20):3529-3532.
Kohler et al., "Highly active palladium/activated carbon catalysts for Heck reactions: correlation of activity, catalyst properties, and Pd leaching", Chem. Feb. 2, 2002 8(3):622-631.
Leblond et al., "Activation of Aryl Chlorides for Suzuki Cross-Coupling by Ligandless, Heterogeneous Palladium" Org. Lett. May 17, 2001 3(10):1555-1557.
Marck et al., "Aryl couplings with heterogeneous palladium catalysts", Tetrahedron Lett. May 16, 1994 35(20):3277-3280.
Mori et al., "Pd(OH)2/C (Pearlman's catalyst): a highly active catalyst for Fukuyama, Sonogashira, and Suzuki coupling reactions", J. Org. Chem. Feb. 21, 2003 68(4):1571-1574.
Shieh et al., "A simple, recyclable, polymer-supported palladium catalyst for suzuki coupling—an effective way to minimize palladium contamination", Synth. Commun. 2002 32(7):1059-1067.
Krauter et al., "Process for carrying out C-C coupling reactions", Abstract of European Patent No. 1,186,583, Mar. 13, 2002.

*Primary Examiner*—Thuan Dinh Dang
(74) *Attorney, Agent, or Firm*—Arnold S. Milowsky; Howson & Howson LLP

(57) ABSTRACT

The present invention provides methods of coupling carbon-containing compounds using a transition metal or transition metal complex on a solid support. The solid support can include alkaline earth metal salts, including carbonate and sulfate salts. The transition metals can include palladium or nickel metal. The method can include combining two carbon containing compounds and a transition metal or transition metal complex on a solid support in the presence of a solvent, desirably an alcohol.

17 Claims, No Drawings

CARBON-CARBON CROSS COUPLING CATALYZED BY TRANSITION METALS ON SOLID SUPPORTS

CROSS-REFERENCE TO RELATED APPLICATIONS

This application claims the benefit of the priority of U.S. Provisional Patent Application No. 60/524,554, filed Nov. 24, 2003.

BACKGROUND OF THE INVENTION

The present invention relates to heterogeneous catalysts that are useful for coupling carbon-containing compounds.

Homogenous catalysts containing solubilizing ligands have been used for coupling carbon-containing compounds and generally have high catalytic activity and give high yields of the desired products. Removal of the catalyst after its use in the reaction can however be quite difficult, especially on an industrial scale. The ligands of the homogeneous catalyst can dissociate from the catalyst and can be difficult to remove, thereby creating purification problems. Laborious workups, scavengers, and crystallizations must therefore be used to remove and/or reduce the presence of the catalyst and/or free ligands to acceptable levels.

In an effort to avoid the use of homogeneous catalysts, heterogeneous catalysts have been utilized to couple carbon-containing compounds. A variety of heterogeneous catalysts is known in the art and includes metals on solid supports. Heterogeneous catalysts are usually inexpensive, commercially available, and exhibit minimal leaching of the metal from the solid support, thus simplifying purification. Examples of commercially available heterogeneous catalysts include palladium metal on silica gel, activated carbon, and polymers.

However, some of these catalysts are expensive and often not available in bulk quantities. Further, palladium on carbon supports, including activated carbon, can be difficult to use since the reaction mixtures tend to turn black, thereby obscuring any reaction changes that can occur during the reaction. It is also difficult to remove the carbon support from the equipment utilized to perform the reaction.

What is needed in the art are alternative homogenous catalysts for coupling carbon-containing compounds that can be easily removed from the reaction mixture.

SUMMARY OF THE INVENTION

In one aspect, methods of coupling carbon-containing compounds are provided.

In a further aspect, methods of coupling carbon-containing compounds are provided using transition metals on solid supports including carbonate and sulfate salts.

In another aspect, methods of preparing bi-aryl compounds are provided.

In yet a further aspect, methods of coupling an aryl compound with a compound having a vinyl group are provided.

In still another aspect, methods of coupling a compound having an alkyl group with a compound having a vinyl group are provided.

In a further aspect, methods of coupling a compound having a thiolactone group and a compound having an alkyl zinc iodide are provided.

In another aspect, methods of coupling a compound having a thioester and a compound having an alkyl zinc halide are provided.

In still a further aspect, methods of coupling an aryl compound with a compound having an alkynyl compound are provided.

In yet another aspect, kits for coupling carbon-containing compounds are provided.

Other aspects and advantages of the present invention are described further in the following detailed description of the preferred embodiments thereof.

DETAILED DESCRIPTION OF THE INVENTION

The present invention provides methods for coupling carbon-containing compounds using transition metals on solid supports including carbonates or sulfates. Desirably, the sulfates or carbonates are salts of Group II metals, i.e., the alkaline earth metals, and the transition metals include palladium and nickel metal, among others. In one embodiment, the present invention provides methods of coupling aryl compounds, however other carbon-containing compounds can be coupled according to the present invention as described in further detail below.

I. Definitions

As used herein, the term "coupling" describes the joining of two chemical compounds by the reactions described herein. Preferably, coupling refers to the joining of two carbon-containing compounds, whereby the compounds are joined together at a carbon atom on each compound.

In one embodiment, the carbon-containing compounds contain leaving groups attached to the carbon-atoms to be coupled. The term "leaving group" refers to a first substituent that is present on a chemical compound, but is displaced by another group. The particular leaving group utilized is dependent upon the specific reaction taking place and can readily be determined by one of skill in the art. Common leaving groups include, without limitation, atoms such as halides, triflates (OTf), boron moieties including boronic acids and trihaloborate salts such as trifluoroborate salts ($BF_3^-$), zinc halides, magnesium moieties, diazonium salts ($N_2^+$), tosylates (OTs), mesylates (OMs), and copper moieties, among others. One of skill in the art would readily recognize the reactivity of a leaving group performing the coupling of the present invention. Typically, the leaving group of one carbon-containing compound differs from the leaving group of the second carbon-containing compound.

Preferably, the leaving group of one carbon-containing compound is a boronic acid. Even more preferably, the leaving group of one carbon-containing compound is a boronic acid and the leaving group of the other carbon-containing compound is a halide. One of skill in the art would readily be able to determine the leaving groups present on the carbon-containing compounds in order for the same to be coupled according to the present invention.

In another embodiment, the carbon-containing compounds joined according to the present invention can already contain carbon-atoms that are sufficiently reactive as to permit coupling according to the present invention, thereby eliminating the requirement for the carbon-containing compound to have a leaving group attached thereto. Typically, one carbon-containing compound has a reactive carbon-atom that is coupled with another carbon-containing compound that contains a carbon-atom having a leaving group attached thereto. The leaving group of one carbon-containing compound and the reactive carbon-atom on the other carbon-containing compound thereby permits coupling of the two carbon-containing compounds. For example, alkenes such as vinyl compounds, alkynes, lactones, and esters can be coupled according to the present invention without requiring that a leaving group is attached thereto. Specifically, the carbon-atom that forms part of the double bond of the alkene or alkyne couples to the second carbon-containing compound according to the present invention. Similarly, the carbon-atom of the carbonyl group of the lactone or ester couples to the second carbon-containing compound according to the present invention. Typically, the carbon-containing compound containing a reactive carbon-atom couples with a second carbon-containing compound having a leaving group attached thereto.

The term "alkaline earth metal" describes any metal in Group II of the periodic table and includes beryllium (Be), magnesium (Mg), calcium (Ca), strontium (Sr), and barium (Ba). Preferably, the alkaline earth metal is Ca, Ba, or Sr and more preferably, the alkaline earth metal is Ca.

As used herein, the term "transition metal" describes any metal in Groups III through XII of the periodic table. Desirably, the transition metal is a Group X metal including Pd or Ni. The transition metal can be present in an unreduced state, i.e., having ligands, such as halides or hydroxyl groups, bound to the metal. Alternatively, the transition metal can be present in a reduced state, i.e., in a zero-valent state and having no ligands bound to the metal. See, Hassan et al., Chem. Rev., 203:1359-1469 (2002).

The term "carbonate" is used herein to refer to a "$CO_3^{2-}$" group. The term "sulfate" is used herein to refer to a "$SO_4^{2-}$" group.

The term "alkyl" is used herein to refer to both straight- and branched-chain saturated aliphatic hydrocarbon groups having 1 to about 10 carbon atoms, and desirably about 1 to about 8 carbon atoms. The term "alkenyl" is used herein to refer to both straight- and branched-chain alkyl groups having one or more carbon-carbon double bonds and containing about 2 to about 10 carbon atoms. Desirably, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bonds and having 2 to about 8 carbon atoms. Desirably, the term alkynyl refers to an alkyl group having 1 or 2 carbon-carbon triple bonds and having 2 to about 6 carbon atoms.

The term "cycloalkyl" is used herein to refer to an alkyl group as previously described that is cyclic in structure and has about 4 to about 10 carbon atoms, and desirably about 5 to about 8 carbon atoms.

The terms "substituted alkyl", "substituted alkenyl", and "substituted alkynyl" refer to alkyl, alkenyl, and alkynyl groups, respectively, having one or more substituents including, without limitation, halogen, CN, OH, $NO_2$, amino, aryl, heterocyclic, alkoxy, aryloxy, alkylcarbonyl, alkylcarboxy, and arylthio which groups can be optionally substituted. These substituents can be attached to any carbon of an alkyl, alkenyl, or alkynyl group provided that the attachment constitutes a stable chemical moiety.

The term "aryl" as used herein refers to an aromatic system which can include a single ring or multiple aromatic rings fused or linked together where at least one part of the fused or linked rings forms the conjugated aromatic system. The aryl groups can typically have from 6 to 20 or more carbon atoms and can include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. Desirably, a substituted aryl group is substituted with 1 to about 4 substituents.

The term "heterocyclic" as used herein refers to a stable 4- to 20 (e.g., 7)-membered monocyclic or multicyclic (e.g., bi- or tri-cyclic) heterocyclic ring which is saturated, partially unsaturated, or wholly unsaturated. The heterocyclic ring has carbon atoms and one or more heteroatoms including nitrogen, oxygen, and sulfur atoms. Preferably, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings, e.g., 2, 3, or 4 rings, in which a heterocyclic ring or rings is fused to an aryl ring. The heterocyclic ring can be attached to the aryl ring through a heteroatom or carbon atom provided the resultant heterocyclic ring structure is chemically stable. Such fused rings can typically have from 8 to 27 or more ring members.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benzazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" as used herein refers to a heterocyclic group having one or more substituents including halogen, CN, OH, $NO_2$, amino, alkyl, cycloalkyl, alkenyl, alkynyl, alkoxy, aryloxy, alkyloxy, alkyicarbonyl, alkylcarboxy, aminoalkyl, and arylthio, which groups can be optionally substituted. Preferably, a substituted heterocyclic group is substituted with 1 to about 4 substituents.

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "alkyloxy" as used herein refers to the alkylOH group, i.e., a "hydroxyalkyl" group, where the point of attachment is through the alkyl group.

The term "arylthio" as used herein refers to the S(aryl) group, where the point of attachment is through the sulfur-atom and the aryl group can be optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

The term "vinyl" refers to a —CH=CH$_2$ group and can be bound to any group that can forms a stable bond to the vinyl moiety.

The term "ester" refers to a —C(O)O— group, which is substituted at both the carbon and oxygen atoms. The oxygen atom of the ester group can be replaced with a sulfur atom, thereby forming a "thioester", i.e., —C(O)S— group.

The term "lactone" refers to a ring (e.g., of 5-15 ring atoms) having an ester moiety in the backbone of the ring. The lactone ring can be optionally substituted with any substituent that forms a stable bond to the ring. The oxygen atom of the ester group can be replaced with a sulfur atom, selenium atom, or tellurium atom thereby forming a "thiolactone", i.e., —C(O)S— group, "selenolactone", i.e., —C(O)Se— group, or "tellurolactone", i.e. —C(O)Te— group.

The term "ligand" as used herein refers to a substituent that is bound to a transition metal.

II. Methods of the Invention

The present invention therefore provides methods of coupling carbon-containing compounds. The coupling reactions are performed using transition metals on solid supports including carbonates or sulfates.

According to the present invention, two carbon-containing compounds can be coupled. Desirably, the carbon-containing compounds contain leaving groups attached thereto. Alternatively, one carbon-containing compound contains a carbon-atom having leaving group attached thereto and couples with a second carbon-containing compound having a carbon-atom that reacts with the carbon-atom of the first carbon-containing compound.

A variety of carbon-containing compounds can be coupled using the method of the present invention and include aryl compounds, vinyl compounds, alkyne compounds, alkyl compounds, lactones including thiolactones, and esters including thioesters, selenoesters, and telluroesters. The carbon-containing compounds can have the same molecular backbone or the molecular backbone of the carbon-containing compounds can differ. The carbon-containing compounds can also be optionally substituted.

The carbon-containing aryl compounds can be, without limitation, an aryl halide such as an aryl bromide, aryl boronic acid, aryl trihaloborate salt such as an aryltrifluoroborate salt, aryl zinc halide, aryl diazonium salt, aryl tosylate, aryl mesylate, aryl cuprate, aryl magnesium complex, or aryl triflate. The carbon-containing vinyl compound can be any vinyl compound that contains a hydrogen atom and can include, without limitation, styrene. The carbon-containing alkynyl compound can be any alkynyl compound that contains a hydrogen atom and can include, without limitation, acetylene.

The carbon-containing compounds are coupled together at carbon-atoms having leaving groups bound thereto. The leaving groups of the carbon-containing compounds can be the same or can differ. Typically, the leaving group of one carbon-containing compound differs from the leaving group of the second carbon-containing compound. A variety of leaving groups can be attached to the carbon-containing compounds and include those previously recited. However, the use of the particular leaving group(s) is not a limitation on the present invention.

Carbonate or sulfate salts, i.e., carbonates or sulfates, are preferably utilized as the support(s) in the present invention and include salts of metals. Typically, the carbonates and sulfates are salts of Group I or II metals, i.e., alkali and alkaline earth metals, respectively. Desirably, the carbonates and sulfates are salts of alkaline earth metals. Typically, the alkaline earth metal salts include, without limitation, calcium carbonate or sulfate ($CaCO_3$ or $CaSO_4$), barium carbonate or sulfate ($BaCO_3$ or $BaSO_4$), or strontium carbonate or sulfate ($SrCO_3$ or $SrSO_4$).

The transition metals are bound to the carbonate or sulfate supports using techniques known to those of skill in the art. Alternatively, the transition metal or transition metal complex bound to the support can be purchased commercially and utilized according to the present invention.

A variety of transition metals can be used in the present invention and include Pd and Ni metals, among others, as described in detail above. The transition metal, including the Pd or Ni metal, can be present on the support in reduced or unreduced forms.

When present in an unreduced form, the transition metal is substituted with ligands. Several ligands can be bound to the transition metal and include, without limitation, acetate, hydroxyl, nitrile, halide, and phosphine substituents. Many transition metal complexes containing such ligands are commercially available and include those heterogeneous catalysts recited on the Strem website at www.strem.com.

When present in a reduced form, the transition metal is not substituted with ligands and is bound to the solid support as the zero-valent metal.

The reducing power of the catalyst can be optionally weakened depending on the ease of the coupling to be performed. A number of agents can be used to decrease the reducing power of the catalyst and include lead (Pb) metal and quinoline, among others. Several weakened catalysts are known in the art or can be prepared by one skilled in the art, and include the Lindlar catalyst, i.e., Pd on $BaCO_3$ that has been treated with Pb and quinoline to weaken the Pd/$BaCO_3$ catalyst.

The carbon-containing compounds of the present invention are typically coupled in a solvent. Any solvent that permits coupling of the carbon-containing compounds can be utilized. Desirably, the solvent dissolves the carbon-containing compounds at about room temperature or about the boiling point of the solvent. The solvent can be dehydrated or can contain water. Typically, the solvent includes an alcohol such as ethanol, methanol, or isopropanol. Preferably, the alcohol is ethanol and more preferably, 190 proof ethanol.

The amount of solvent utilized depends upon the scale of the reaction and specifically the amount of carbon-containing compound present in the reaction mixture. One of skill in the art would readily be able to determine the amount of solvent required to couple the carbon-containing compounds.

The solvent can also optionally contain additional components including ethers, water, or mixtures thereof. Typically, the ether is tetrahydrofuran (THF) or diethyl ether. The optional components are preferably present in an amount that does not permit precipitation of the starting materials and/or products.

The present invention therefore provides for combining a first carbon containing compound, a second carbon-containing compound, a transition metal on a solid support comprising an alkaline earth metal salt, and a solvent comprising an alcohol. The carbon-containing components can be combined at room temperature for a period of time sufficient to couple the carbon-containing compounds. One of skill in the art using known techniques would readily be able to monitor the progress of the coupling reaction and thereby determine the amount of time required to perform the reaction.

Alternatively, the combined components can be heated to the boiling point of the solvent. The components are typically heated to a temperature that does not promote decomposition of the carbon-containing compounds or transition metal on the solid support. Typically, the components are heated to the boiling point of the alcohol or mixture of the alcohol. The components are heated for a period of time sufficient to permit the carbon-containing compounds to couple. One of skill in the art using known techniques would readily be able to monitor the progress of the coupling reaction during heating and thereby determine the amount of time required to perform the reaction.

The coupled product can then be isolated using techniques known to those skilled in the art. In one embodiment, the coupled product is soluble in the solvent mixture. Typically, the transition metal on the solid support, i.e., the catalyst, is removed from the mixture using techniques known by those of skill in the art. Such techniques are readily known to one of skill in the art and include, without limitation, filtration, chromatography, and centrifugation. Desirably, the catalyst is removed using filtration. Preferably, the solvent mixture is filtered at temperatures below the boiling point of the solvent, but above room temperature. However, the heated mixture can also be cooled to a lower temperature, such as about room temperature.

In another embodiment, the coupled product is insoluble in the solvent mixture. Water is typically added to the solvent mixture and the temperature of the solvent/water mixture lowered to about room temperature. The solid containing the catalyst, coupled product, and inorganic by-products is collected using any of the above-noted techniques, preferably including filtration. The resultant solid is then combined in a second solvent, including tetrahydrofuran, and heated. The second solvent must dissolve the coupled product at either room or elevated temperatures. The coupled product can be isolated from the hot solvent mixture using filtration.

The carbon-containing coupled product can then be isolated from the solvent mixture as a solid by precipitation, crystallization, or by removing the solvent from the mixture. Typically, the solvent is removed from the mixture by evaporating the solvent. Evaporation can be performed at any temperature that does not promote decomposition of the coupled product. Desirably, evaporation of the solvent is performed at a temperature of about room temperature or above. Vacuums can also be utilized to promote evaporation of the solvent. Typically, vacuums of less than about 1 atmosphere (atm) can be utilized.

The solid carbon-containing coupled product can also be optionally dried to remove residual solvent. Typically, drying is performed under vacuums of less than about 1 atm for a period of at least about 6 hours. Preferably, the drying is performed for periods of about 6 hours to about 24 hours.

In one embodiment, the method includes coupling two optionally substituted aryl compounds to form a compound whereby the aryl groups are directly bound together. Typically, the leaving group bound to a carbon-atom of the first carbon-containing compound differs from the leaving group bound to a carbon-atom of the second carbon-containing compound. Desirably, one aryl compound is an optionally substituted aryl halide, preferably an aryl bromide, and one aryl compound is an optionally substituted aryl boronic acid. See, Scheme I.

In another embodiment, the method includes coupling one carbon-containing compound having a leaving group attached thereto and a carbon-containing compound containing a vinyl group. Desirably, the method includes coupling an optionally substituted aryl compound, such as an aryl halide, and a compound containing a vinyl group. Preferably, the aryl halide is an aryl bromide. The product thereby provides a compound whereby the aryl group is directly attached to the carbon-atom of the vinyl group.

In a further embodiment, the method includes coupling an optionally substituted alkyl compound, such as an alkyl halide, and a compound comprising a vinyl group. Preferably, the alkyl halide is an alkyl bromide. The product provides a compound whereby the aryl group is directly attached to the carbon-atom of the alkyl group which was bound to the halide group.

SCHEME 1

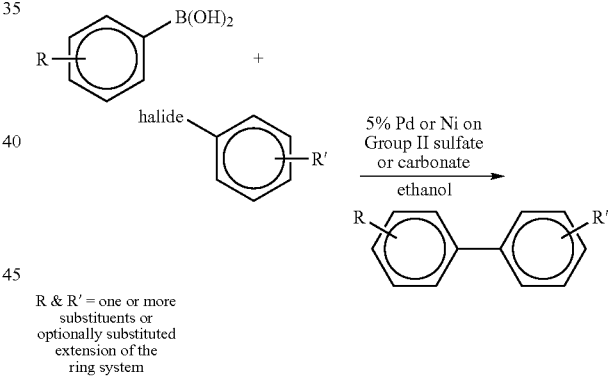

R & R' = one or more substituents or optionally substituted extension of the ring system In yet another embodiment, the method includes coupling a carbon-containing compound having a leaving group attached thereto and an alkyne. Desirably, the method includes coupling an optionally substituted aryl compound, such as an aryl halide, and an alkynyl compound. Preferably, the aryl halide is an aryl bromide. The product thereby provides a compound whereby the aryl group is directly attached to the carbon-atom of the alkyne.

In still a further embodiment, the method includes coupling a lactone and a carbon-containing compound having a leaving group attached thereto. Desirably, the method includes coupling a lactone and an alkyl compound, such as an alkyl zinc halide. Preferably, the alkyl zinc halide is an alkyl zinc iodide, alkyl zinc chloride, or alkyl zinc bromide, and the lactone is a thiolactone. The product thereby provides a compound whereby the alkyl group is directly attached to the carbon-atom of the carbonyl of the lactone.

In yet another embodiment, the method includes coupling a thioester and a carbon-containing compound having a leaving group attached thereto. Desirably, the method includes coupling a thioester and an alkyl compound, such as an alkyl zinc halide. The product thereby provides a ketone compound whereby the alkyl group is directly attached to the carbon-atom of the thiocarbonyl of the thioester.

In one preferred embodiment, the present invention provides a method of coupling carbon-containing compounds comprising the steps of combining an aryl boronic acid, an aryl halide, a first solvent comprising an alcohol, and palladium or nickel metal on a solid support comprising barium sulfate or calcium carbonate; heating the combined reagents; filtering the heated product; evaporating the solvent from the filtered product; and drying the evaporated product.

In another preferred embodiment, the present invention provides a method of preparing bi-aryl compounds including combining an aryl boronic acid, an aryl halide, palladium or nickel metal on a solid support comprising an alkaline earth metal salt, and a solvent to form a mixture. The method can also include one or more steps including heating the mixture; diluting the heated solution with a second solvent; filtering the diluted solution; evaporating the first and second solvents from the filtered solution to form a solid; washing the solid; or drying the washed solid.

III. Kits of the Invention

Kits for coupling carbon-containing compounds are also provided according to the present invention. Specifically, the kits can contain a solid support of an alkaline earth metal salt and palladium or nickel metal attached thereto and a solvent comprising an alcohol.

The kits can optionally include other solvents that can be utilized to couple the carbon-containing compounds and include ethers or water, including distilled or deionized water.

The kits can also include the carbon-containing compounds to be coupled according to the present invention.

The kit can further contain instructions for performing the coupling reactions. Also provided in a kit can be other suitable chemicals, disposable gloves, decontamination instructions, applicator sticks or containers, and sample preparator cups.

One of skill in the art could assemble any number of kits with the information and components necessary to perform the method of the present invention.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Comparison of Catalysts in the Preparation of 3-chloro-5-(4,4-dimethyl-2-oxo-1,4-dihydro-2H-benzo[d][1,3]oxazin-6-yl)benzonitrile Reactions vessels of a Mettler-Toledo® Bohdan parallel synthesizer were each charged, under a nitrogen blanket, with 3-bromo-5-chlorobenzonitrile (0.42 g, 1.94 mmol), 4,4-dimethyl-2-oxo-1,4-dihydro-2H-benzo[d][1,3]oxazin-6-boronic acid (0.45 g, 2.04 mmol), soda ash (0.23 g, 2.17 mmol), ethanol SDA 3A 190 proof (6 mL), and 0.045 g (1 mol %) of the catalyst set forth in Table 1.

TABLE 1

| Reaction | Catalyst | % Conversion to Product |
|---|---|---|
| 1 | 5% reduced Pd on BaSO$_4$ | 85 |
| 2 | 5% unreduced Pd on BaSO$_4$ | 93 |
| 3 | 5% unreduced Pd on CaCO$_3$ | 95 |

The suspensions were vigorously stirred and heated to 80° C. overnight. After dilution with THF (25 mL), the diluted solutions were analyzed by high performance liquid chromatography (HPLC).

As noted in Table 1, the conversion to the product was about 85% for the reduced Pd catalyst and about 93% or greater for the unreduced Pd catalysts. In this example, unreduced Pd on CaCO$_3$ provided the highest conversion to 3-chloro-5-(4,4-dimethyl-2-oxo-1,4-dihydro-2H-benzo[d][1,3]oxazin-6-yl)benzonitrile.

The solution from reaction 3 was then filtered through a Celite® filter, filtered through an Acrodisc® syringe filter, evaporated to a slurry, thinned with isopropanol, filtered, washed with isopropanol, and dried to give 0.38 g (63% yield) of 3-chloro-5-(4,4-dimethyl-2-oxo-1,4-dihydro-2H-benzo[d][1,3]oxazin-6-yl)benzonitrile.

Example 2

Comparison of Solvents in the Preparation of 3-chloro-5-(4,4-dimethyl-2-oxo-1,4-dihydro-2H-benzo[d][1,3]oxazin-6-yl)benzonitrile Using Pd on Carbonates or Sulfates 4,4-dimethyl-2-oxo-1,4-dihydro-2H-benzo[d][1,3]oxazin-6-boronic acid (0.45 g, 2.04 mmol) was heated with 3-bromo-5-chlorobenzonitrile (0.42 g, 1.94 mmol) in alcohol SDA 3A 190 proof in the presence of soda ash (0.23 g, 2.17 mmol) and 5% Pd on BaSO$_4$ or 5% Pd on CaCO$_3$ to produce 3-chloro-5-(4,4-dimethyl-2-oxo-1,4-dihydro-2H-benzo[d][1,3]oxazin-6-yl)benzonitrile in good yields with good purity.

When the same reaction was performed using tetrahydrofuran (THF) in place of the alcohol, 3-chloro-5-(4,4-dimethyl-2-oxo-1,4-dihydro-2H-benzo[d][1,3]oxazin-6-yl)benzonitrile was produced, but was contaminated with starting materials when 5% Pd on BaSO$_4$ was utilized as the catalyst. When 5% Pd on CaCO$_3$ was utilized as the catalyst, only trace amounts of 3-chloro-5-(4,4-dimethyl-2-oxo-1,4-dihydro-2H-benzo[d][1,3]oxazin-6-yl)benzonitrile were produced.

When the reaction was performed using THF and small amounts (3%) of ethanol, higher conversions of about 40% (5% Pd on BaSO$_4$) and 75% (5% Pd on CaCO$_3$) to 3-chloro-5-(4,4-dimethyl-2-oxo-1,4-dihydro-2H-benzo[d][1,3]oxazin-6-yl)benzonitrile were observed.

Example 3

Comparison of Solvents in the Preparation of 3-chloro-5-(4,4-dimethyl-2-oxo-1,4-dihydro-2H-benzo[d][1,3]oxazin-6-yl)benzonitrile Using Pd on Charcoal 4,4-dimethyl-2-oxo-1,4-dihydro-2H-benzo[d][1,3]oxazin-6-boronic acid (0.45 g, 2.04 mmol) was heated with 3-bromo-5-chlorobenzonitrile (0.42 g, 1.94 mmol) in the presence of soda ash (0.23 g, 2.17 mmol) and the 5% Pd/C catalyst in a solvent to produce 3-chloro-5-(4,4-dimethyl-2-oxo-1,4-dihydro-2H-benzo[d][1,3]oxazin-6-yl)benzonitrile in good yields and purity. See, Table 2.

TABLE 2

| 5% Pd/C Catalyst | Solvent | % Conversion to Product |
|---|---|---|
| Degussa's Pd/C E1002 SU/W | methanol | 97 |
| | ethanol SDA 3A | 92 |
| | isopropanol | 88 |
| | aqueous THF | 34 |

The inventor also noted that when the reactions were run in methanol, impurities were produced. Without wishing to be bound by theory, the inventor has hypothesized that the impurities were produced by the addition of methanol to the nitrite moiety in both the starting material and product.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method of coupling carbon-containing compounds comprising combining (i) a first carbon containing compound, with (ii) a second carbon-containing compound, in the presence of (iii) palladium or nickel metal on a solid support comprising an alkaline earth metal salt, and (iv) a solvent comprising an alcohol, wherein said first carbon-containing compound is an aryl halide and said second carbon-containing compound is an aryl boronic acid and the product of said coupling is a bi-aryl compound.

2. The method according to claim 1, wherein said alkaline earth metal salt is a calcium salt.

3. The method according to claim 2, wherein said calcium salt is calcium sulfate or calcium carbonate.

4. The method according to claim 1, wherein said alkaline earth metal salt is a barium salt.

5. The method according to claim 4, wherein said barium salt is barium sulfate.

6. The method according to claim 1, wherein said alkaline earth metal salt is a strontium salt.

7. The method according to claim 6, wherein said strontium salt is strontium carbonate.

8. The method according to claim 1, wherein said palladium or nickel metal is reduced.

9. The method according to claim 1, wherein said palladium or nickel metal is unreduced.

10. The method according to claim 1, wherein said solvent is ethanol, methanol, or isopropanol.

11. The method according to claim 10, wherein said solvent is ethanol.

12. The method according to claim 1, wherein said solvent further comprises water.

13. The method according to claim 1, wherein said solvent further comprises an ether.

14. The method according to claim 13, wherein said ether is tetrahydrofuran.

15. The method according to claim 1, further comprising heating said solvent comprising said alcohol, said first carbon containing compound, said second carbon-containing compound, and said palladium or said nickel metal on said solid support comprising an alkaline earth metal salt.

16. The method according to claim 15, further comprising:
    diluting said heated solution with a second solvent;
    filtering said diluted solution;
    evaporating said first and second solvents from said filtered solution to form a solid;
    washing said solid; and
    drying said washed solid.

17. A method of coupling carbon-containing compounds comprising:
    (i) combining an aryl boronic acid, an aryl halide, a first solvent comprising an alcohol, and palladium or nickel metal on a solid support comprising barium sulfate or calcium carbonate;
    (ii) heating the product of step (i);
    (iii) filtering the product of step (ii);
    (iv) evaporating said solvent from the product of step (iii); and
    (v) drying the product of step (iv);
    wherein the product of said coupling is a bi-aryl compound.

* * * * *